(12) United States Patent
Gu et al.

(10) Patent No.: US 11,000,262 B2
(45) Date of Patent: May 11, 2021

(54) MICRO VASCULAR ULTRASONIC CONTRAST IMAGING BY ADAPTIVE TEMPORAL PROCESSING

(71) Applicant: KONINKLIJKE PHILIPS N.V., Eindhoven (NL)

(72) Inventors: Xiaolin Gu, Eindhoven (NL); Yinhui Deng, Eindhoven (NL); Xiaomin Li, Eindhoven (NL); Vijay Thakur Shamdasani, Eindhoven (NL); Ying Wu, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 542 days.

(21) Appl. No.: 15/753,198

(22) PCT Filed: Aug. 19, 2016

(86) PCT No.: PCT/EP2016/069712
§ 371 (c)(1),
(2) Date: Feb. 16, 2018

(87) PCT Pub. No.: WO2017/032715
PCT Pub. Date: Mar. 2, 2017

(65) Prior Publication Data
US 2019/0015074 A1    Jan. 17, 2019

(30) Foreign Application Priority Data
Aug. 21, 2015    (WO) ................ PCT/CN2015/087789
Oct. 15, 2015    (EP) ..................................... 15189930

(51) Int. Cl.
*A61B 8/08*        (2006.01)
*A61B 8/06*        (2006.01)
(Continued)

(52) U.S. Cl.
CPC ................ *A61B 8/481* (2013.01); *A61B 8/06* (2013.01); *A61B 8/085* (2013.01); *A61B 8/5223* (2013.01);
(Continued)

(58) Field of Classification Search
CPC ........... A61B 8/481; A61B 8/06; A61B 8/085; A61B 8/5223; A61B 8/0825; G16H 30/40; G01S 7/52039
See application file for complete search history.

(56) References Cited

U.S. PATENT DOCUMENTS 5,883,613 A    3/1999    Averkiou et al.
6,013,032 A    1/2000    Savord
(Continued)

FOREIGN PATENT DOCUMENTS

WO    2008074889 A1    6/2008
WO    2014061258 A1    4/2014
WO    2014101489 A1    7/2014

OTHER PUBLICATIONS

Gauthier et al "Assessment of Quantitative Perfusion Parameters by Dynamic Contrast Enhanced Sonagraphy Using a Deconvolution Method" Journal of Ultrasound in Medicine, Apr. 2, 2012, p. 595.
Wilson et al "Real Time Temporal Maximum Intensity Projection Imaging of Hepatic Lesions With Contrast Enhanced Sonography" AJR: 190 Mar. 2008.

*Primary Examiner* — Hien N Nguyen

(57) ABSTRACT

An ultrasonic diagnostic imaging system produces contrast enhanced images which are processed differently during different stages of contrast agent wash-in. During an initial stage of contrast wash-in, imaging is done using pixels processed by maximum intensity detection, to better reflect the rapid change in contrast intensity. During a later stage of contrast wash-in, time averaged processing is used to diminish the effects of noise and motion on the pixel values. During an intermediate period of peak enhancement, a combination of both pixel values processed by both tech-
(Continued)

niques is used. In another aspect, a wash-in period can be characterized by an appearance stage, a growth stage and a peak stage, in which contrast pixel data is adaptively processed in different ways during these periods.

12 Claims, 5 Drawing Sheets

(51) Int. Cl.
*G01S 7/52* (2006.01)
*G16H 30/40* (2018.01)

(52) U.S. Cl.
CPC ......... *G01S 7/52039* (2013.01); *G16H 30/40* (2018.01); *A61B 8/0825* (2013.01)

(56) References Cited

U.S. PATENT DOCUMENTS

| | | | |
|---|---|---|---|
| 6,186,950 | B1 | 2/2001 | Averkiou et al. |
| 6,375,617 | B1 | 4/2002 | Fraser |
| 6,436,049 | B1 | 8/2002 | Kamiyama et al. |
| 6,676,606 | B2 | 1/2004 | Simpson et al. |
| 6,692,438 | B2 | 2/2004 | Skyba et al. |
| 2009/0099452 | A1 | 4/2009 | Hashimoto |
| 2009/0204003 | A1 | 8/2009 | Guracar |
| 2010/0060644 | A1 | 3/2010 | Elie et al. |
| 2012/0253190 | A1 | 10/2012 | Gauthier et al. |
| 2013/0116557 | A1* | 5/2013 | Yoshikawa ............ A61B 8/461 600/431 |
| 2015/0297172 | A1 | 10/2015 | Takagi et al. |

* cited by examiner

MICRO VASCULAR ULTRASONIC CONTRAST IMAGING BY ADAPTIVE TEMPORAL PROCESSING

This application is the U.S. National Phase application under 35 U.S.C. § 371 of International Application No. PCT/EP2016/069712, filed on Aug. 19, 2016, which claims the benefit of Application Serial No. PCT/CN2015/087789, filed Aug. 21, 2015 and EP Application Serial No. 15189930.9 filed Oct. 15, 2015. These applications are hereby incorporated by reference herein.

FIELD OF THE INVENTION

This invention relates to medical diagnostic ultrasound systems and, in particular, to ultrasound systems which perform contrast-enhanced imaging studies to visualize blood flow in tissue micro-vasculature.

BACKGROUND OF THE INVENTION

Ultrasonic contrast agents have been used for a number of years to diagnose disease states from the enhancement the agents provide to blood flow. Blood cells are very small and are poor reflectors of ultrasound, generally providing little information for ultrasonic imaging. However, microbubble contrast agents in the blood stream are highly reflective of ultrasound which can be segmented by their harmonic response, enabling greatly enhanced images of blood flow characteristics. One use of contrast agents has been to visualize the flow or perfusion of tissue micro-vasculature. Recent studies of lesions such as breast lesions have focused on the structure, flow characteristics, and extent of the micro vasculature supporting the lesion. Early detection of breast lesions and definition of the lesion boundaries can often be ascertained by using ultrasound to look for characteristic vascular structures. In addition, changes in lesion growth and development such as those resulting from chemotherapy often manifest themselves at an early point in time by changes in the lesion vasculature. It is anticipated that these studies may be aided by the use of contrast agents. However, the vascular structures involved are tiny, micro-vascular structures with individual vessels conducting minute amounts of blood flow at very low rates of flow, making them difficult to clearly discern in an ultrasonic image. One development that aids in this process is the use of contrast agents to visualize the flow of individual microbubbles through micro vasculature that is described in U.S. Pat. No. 6,676,606 (Hope Simpson et al.) The system described in this patent, images microbubbles of a contrast agent that are introduced into the body in either a bolus injection or by a continuous infusion with intermittent high mechanical index flash transmission used to periodically destroy the microbubbles in the image region, allowing newly perfusing microbubbles to be observed as they arrive in the vascular system flow. A persistence processor is used which identifies the current positions of microbubbles through a temporal maximum intensity projection, then persists their appearance in the micro vasculature as they progressively move through the micro vasculature from frame to frame. The images that are produced will thus capture the trajectories of microbubbles as they travel through the tissue and hence the paths of micro vessels in the image region. The technique allows the visualization of both the intratumoral vasculature and vessel-tree structure, providing more pathophysiological information that can facilitate clinicians to make better decisions.

However, the inventors of the present invention have recognized that the contrast enhancement of micro vascular structures resulting from the wash-in of contrast agents is a dynamic process with diverse characteristics at different stages of the buildup and then decline of the concentration of microbubbles in the micro blood vessels. During the early stage of the wash-in of the contrast agent, larger vessels are enhanced as they contain blood flow with higher velocity. In order to capture the fast-moving trajectories of contrast agents within larger vessels, it is preferred to use the temporal maximum intensity projection method of Hope Simpson et al., which is sensitive to the movement of contrast agents and the resulting rapid change of the contrast enhancement. At this stage of the wash-in, the presence of signal noise leading to the appearance of image artifacts is not great. But at later stages of the wash-in of the contrast agent, an increasing number of micro vessels with slow blood flow fill with microbubbles and are enhanced. The effects of signal noise now accumulate, and an improvement of the signal-to-noise ratio rather than high sensitivity to change becomes more important for the visualization of rich and detailed micro vasculature. In addition, uncompensated motion artifacts which can be caused by either the heartbeat or breathing can form and accumulate as time elapses. A processing method which responds to the change of conditions in the later stages of wash-in by suppressing motion artifacts and noise in the signals is preferred. Accordingly it is an object of the present invention to provide an ultrasound system for contrast enhanced micro vascular imaging which adapts it processing for these and/or other changing conditions.

The publications US2010/060644A1 by Nicolas Elife et al., Assessment of Quantitative Perfusion Parameters by Dynamic Contrast Enhanced Sonagraphy Using a Deconvolution Method by Marianne Gauthier et al., WO2014/061258A1 by Takagi Kazuya and US2012/0253190A1 by Thomas Patrice jean Arsene Gauthier et al. are all related to quantification of perfusion curves or parameters such as time intensity curves and/or extracting one or more features from a contrast enhanced ultrasound image, but none of them is related to an improvement in providing the contrast enhanced ultrasound image.

SUMMARY OF THE INVENTION

In some aspects, the present invention provides ultrasonic diagnostic imaging systems and methods for contrast enhanced imaging of micro vasculature in an image region. The ultrasound system can include, for example, an ultrasound probe configured to transmit ultrasonic beams and receive ultrasonic echo signals, a beamformer configured to beamform the echo signals to produce coherent echo signals, a signal separator responsive to the coherent echo signals and configured to produce separated harmonic echo signals received from a contrast agent, a contrast temporal processor, responsive to the harmonic echo signals, and configured to process harmonic signals received from a contrast agent to produce a contrast data value for each of a plurality of spatial locations in the imaging region for a time point in a time period, a scan converter coupled to receive the produced contrast data values and configured to produce a contrast image for the time point by arranging the produced contrast data values for the plurality of spatial locations for the time point in a desired image format, and a display coupled to the scan converter which displays a contrast image, wherein the contrast value for a spatial location in the image region is produced in different ways over the time period, and the time period includes at least a wash-in stage of the contrast agent. In other words, over the time period, given a first time point and a second time point different from the first time point, the contrast temporal processor can be configured to produce a contrast value for the first time point in a way different from the way to produce a contract value for the second time point. Unlike the conventional approaches of using a same way of temporal maximum intensity projection to produce contrast images, the contrast images over a time period, such as a temporal sequence of contrast images, are produced in different ways over the time period. Hence, it enables applying different processing ways to produce a contrast image for different certain time points so as to improve the contrast images by adapting the processing in accordance with different sub-periods of a time period, such as different stages of the perfusion of the contrast agent.

An ultrasound image of a region is known as comprising ultrasound data values of the region arranged in accordance with the spatial locations. In other words, each pixel or voxel of the ultrasound image represents an ultrasound data value of a corresponding spatial location. There are various types of ultrasound images, such as a B-mode ultrasound image, a Doppler ultrasound image, a contrast ultrasound image (also called contrast image, or contrast enhanced image) etc. Ultrasound data values in various types of ultrasound images represent various physical parameters. For example, the pixel value in a B-mode ultrasound image represents the intensity of the ultrasound echo signal reflected by tissues. For example, the pixel value in a Doppler ultrasound image represents the Doppler effect caused by moving tissues such as a blood flow. For example, the pixel value in a contrast image represents the amount of a contrast agent. In some embodiments, the contrast temporal processor can include a maximum intensity detector and a time averaged calculator which process the harmonic echo signals to produce differently processed contrast data values. Maximum intensity detection can better reflect the rapid change in contrast intensity, and time averaged processing can reduce the effects of noise and motion on the pixel values. In some other embodiments, either or both of the maximum intensity detector and the time average calculator can be replaced by other existing or future-developed calculator(s) or detector(s).

The contrast temporal processor can also include an MI weighting circuit configured to weight contrast data values produced by the maximum intensity detector, and a TA weighting circuit configured to weight contrast data values produced by the time averaged calculator. The contrast temporal processor can include a summer configured to sum the weighted contrast data values, and/or a frame buffer configured to store frames of harmonic echo signals received from the signal separator. In certain aspects, the contrast temporal processor can include a time-intensity curve trigger circuit, responsive to harmonic echo signals from the frame buffer, and configured to produce a time-intensity curve of successive stages of contrast wash-in. In some aspects, the time-intensity curve demarcates an initial wash-in stage and a later wash-out stage, and the time-intensity curve is configured to trigger the weighting circuits to produce maximum intensity contrast values during the initial stage and time averaged contrast values during the later stage. Alternatively, the time-intensity curve further demarcates an intermediate stage following the initial stage, and the time-intensity curve is configured to trigger the weighting circuits to produce maximum intensity contrast values and time averaged contrast values during the intermediate stage, and the summer is configured to produce a combination of the maximum intensity contrast values and the time averaged contrast values during the intermediate stage. In some aspects, the time-intensity curve demarcates an appearance stage, a growth stage, and a peak stage, and the time-intensity curve triggers the weighting circuits to produce maximum intensity contrast values during the appearance stage, time averaged contrast values during the peak stage, and a mixture of maximum intensity contrast values and time averaged contrast values during the growth stage.

In some aspects, the MI weighting circuit is configured to utilize a declining weighting function during the intermediate stage, and the TA weighting circuit is configured to utilize an increasing weighting function during the intermediate stage. The contrast temporal processor can also include a T-I history buffer configured to store parameters of a T-I curve produced by the time-intensity curve trigger circuit. In some aspects, the time-intensity curve trigger circuit is configured to use parameters stored during a first contrast wash-in period to trigger the weighting circuits during a second contrast wash-in period. The parameters can include a first parameter $t_2$ demarcating the end of an initial wash-in stage and a second parameter $t_3$ demarcating the beginning of a later wash-out stage.

In certain aspects, the signal separator is further configured to separate fundamental frequency echo signals, and the system further includes a B mode detector responsive to fundamental frequency echo signals and configured to produce detected B mode signals, and a scan converter responsive to the detected B mode signals and configured to produce a B mode image in the desired image format. The system can further include an image processor, responsive to the contrast image and the B mode image, and configured to produce an image including a combination of the B mode image and the contrast image.

As described further herein, the present invention includes ultrasound systems and methods. In some aspects, the ultrasound systems include various structures standard in computers, such as microprocessors, integrated circuits, (e.g., FPGAs), memory, hard drives, etc. In some embodiments, the present invention includes ultrasound systems having instructions thereon, which, when executed, cause the system to carry out the various steps and functions described herein. For example, the present invention includes ultrasonic diagnostic imaging systems for contrast enhanced imaging of micro vasculature having instructions thereon, which, when executed, cause the system to perform the following steps: transmit, with an ultrasound probe, ultrasonic beams and receive ultrasonic echo signals; beamform the echo signals to produce coherent echo signals; separate harmonic echo signals received from a contrast agent; process the harmonic signals received from a contrast agent in different ways over a time period including at least a wash-in stage of the contrast agent; produce a contrast image in a desired image format; and a display coupled to the scan converter which displays a contrast image.

In accordance with another aspect of the present invention, it is provided with an apparatus for producing an ultrasound contrast image of micro vasculature in an image region, which comprises: a contrast temporal processor responsive to harmonic echo signals received from a contrast agent and configured to process harmonic signals received from a contrast agent to produce a contrast data value for each of a plurality of spatial locations in the image region, and a scan converter coupled to receive the produced contrast data values and configured to produce a temporal sequence of contrast images over a time period, wherein the contrast value for a spatial point location is produced in different ways over the time period including at least a wash-in stage of the contrast agent. The apparatus can be further coupled to a display for displaying the contrast image. Additionally or alternatively, such system can comprise a display for displaying the contrast image. The apparatus can be coupled to an apparatus or system for providing harmonic echo signals received from a contrast agent. Additionally or alternatively, the apparatus can be part of an apparatus or system for providing harmonic echo signals received from a contrast agent. The provided harmonic echo signals can be a sequence of frames of harmonic echo signals. The provided harmonic echo signals can be a sequence of contrast data frames produced in accordance with the conventional approaches where the contrast data frames are produced in the same way over the time. An apparatus or system for providing harmonic echo signals received from a contrast agent can comprise an ultrasound probe configured to transmit ultrasonic beams and receive ultrasonic echo signals, or it can be any information system configured to store data such as contrast-enhanced ultrasound data, such as Hospital Information System (HIS), a picture archiving and communication system (PACS), an electronic medical record information (EMR) system or the like.

DETAILED DESCRIPTION OF THE EMBODIMENTS

In accordance with some embodiments of the present invention, a diagnostic ultrasound system and method are described which enable a user to image micro vasculature with a contrast agent. The contrast pixel data is adaptively processed in different ways as the contrast agent washes in and then washes out of the microvasculature. The systems and methods of the present invention vary processing adaptively to provide the most beneficial image processing during each stage of contrast perfusion.

In some embodiments, the contrast pixel data is adaptively processed in different ways during three periods: a wash-in period, an enhancement stabilization or intermediate period, and a wash-out period. For example, maximum intensity detection is used during the early stage of wash-in to better enhance the rapid buildup of contrast. During the later wash-out stage, time-averaged processing of the temporal image data is used to reduce noise and motion artifacts. During an intermediate peak enhancement stage, a combination of both of these techniques is used, changing from maximum intensity detection to time-averaged processing during this period.

In certain embodiments, a wash-in period can be characterized by an appearance stage, a growth stage and a peak stage, in which contrast pixel data is adaptively processed in different ways during these periods. Here, maximum intensity detection can be used during the appearance stage to better enhance the rapid buildup of contrast. During the later peak stage, time-averaged processing of the temporal image data is used to reduce noise and motion artifacts. During the growth stage, a combination of both of these techniques is used, changing from maximum intensity detection to time-averaged processing during this period.

Figure 1:
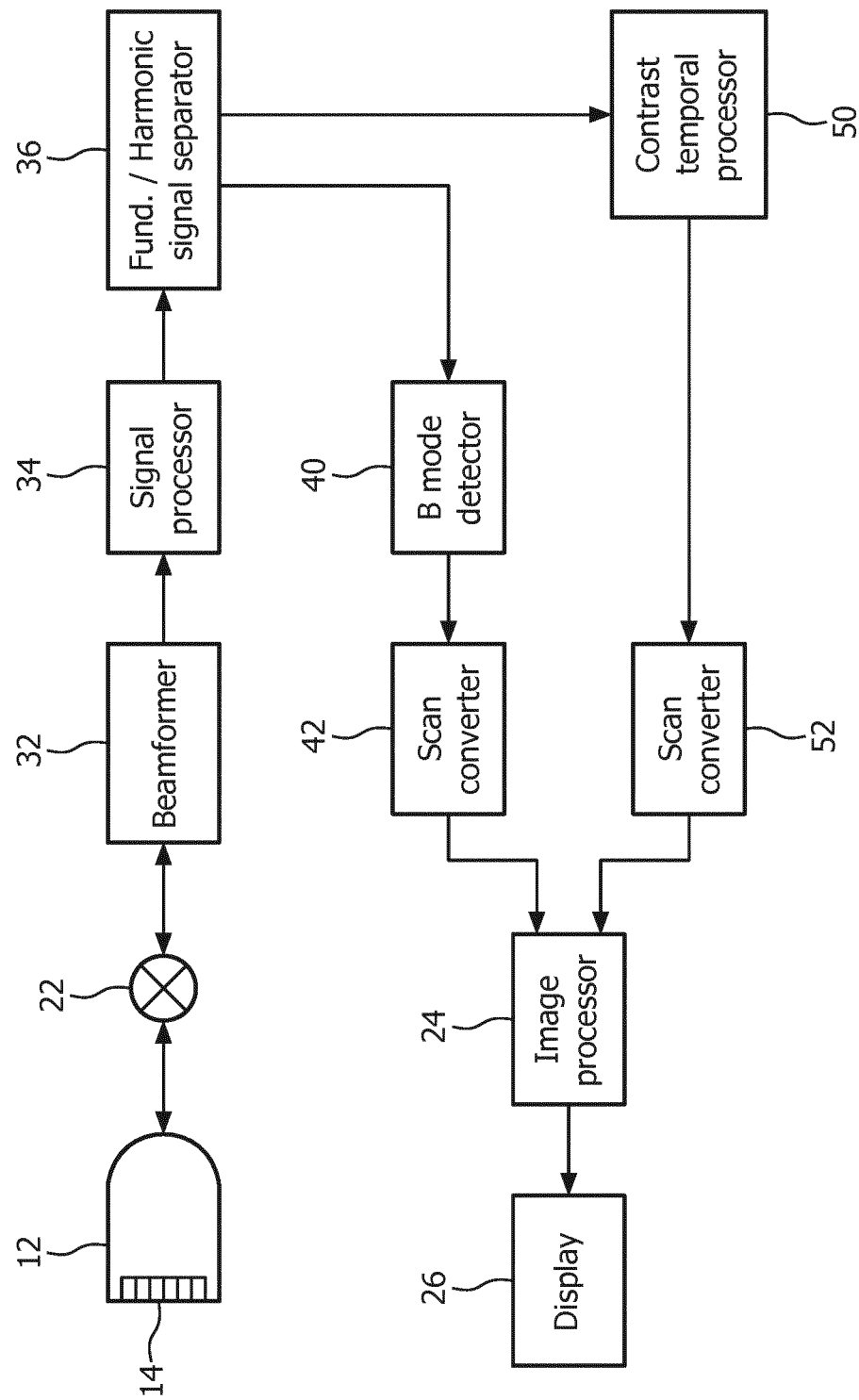
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. An ultrasonic probe 12 includes an array 14 of ultrasonic transducer elements that transmit and receive ultrasonic pulses. The array may be a one-dimensional linear or curved array for two-dimensional imaging, or may be a two-dimensional matrix of transducer elements for electronic beam steering in three dimensions. The array may also be a one-dimensional array that is mechanically swept back and forth by the probe to scan a three-dimensional volume of the body. The ultrasonic transducers in the array 14 transmit ultrasonic energy and receive echoes returned in response to this transmission. A transmit/receive ("T/R") switch 22 is coupled to the ultrasonic transducers in the array 14 to selectively couple signals from the transducer elements to a beamformer 32 during the receive phase of operation. The times at which the transducer array is activated to transmit signals is also controlled by the beamformer 32 so that a focused and steered beam is transmitted from the array during the transmit phase of the pulse-echo sequence of operation.

Echoes from the transmitted ultrasonic energy are received by the transducer elements of the array 14, which generate echo signals that are coupled through the T/R switch 22 and digitized by analog to digital ("A/D") converters at the input of the beamformer when the system uses a digital beamformer. Analog beamformers may alternatively be used. Control of the ultrasound system and of various control settings for imaging such as probe selection is effected by user manipulation of the controls of a control panel which is coupled to and applies its control through a central system controller (not shown.)

The echo signals received from the individual transducer elements of the array 14 are delayed and summed by the beamformer 32 to beamform coherent echo signals. For 3D imaging with a two-dimensional array, it is preferable to partition the beamformer between a micro-beamformer located in the probe and the main beamformer in the system mainframe as described in U.S. Pat. No. 6,013,032 (Savord) and U.S. Pat. No. 6,375,617 (Fraser). The digital coherent echo signals are then processed by a signal processor 34 which performs operations such as bandpass filtering, speckle reduction, image contrast enhancement, tissue clutter suppression and motion compensation. The signal processor can also shift the received frequency band to a lower or baseband frequency range. In this embodiment, the transmit frequency and the receiver frequency are individually controlled so that the beamformer 32 is free to receive a band of frequencies which is different from that of the transmitted band such as a harmonic frequency band.

Echo signals received during imaging with a contrast agent, such as microbubbles, are coupled to a fundamental/harmonic signal separator 36. The fundamental/harmonic signal separator 36 preferably separates echoes returned from harmonic contrast agents by the pulse inversion technique, in which echoes resulting from the transmission of multiple pulses to an image location are additively combined to cancel fundamental signal components and enhance harmonic components, and subtractively combined to produce fundamental frequency signal components. A preferred pulse inversion technique is described in U.S. Pat. No. 6,186,950 (Averkiou et al.), for instance. The fundamental and harmonic frequencies, such as signal band containing fundamental frequencies f and second harmonic frequencies 2f, can also be separated by bandpass filtering using a lower passband with a peak at the fundamental frequency f and a higher passband with a peak at the second harmonic frequency 2f.

Fundamental frequency signals are coupled to a B mode detector 40 for the formation of a B mode image of the tissue structure being imaged. As is known in the art, the B mode detector performs amplitude detection of the received fundamental frequency echo signals. The detected echo signals are coupled to a scan converter 42 which arranges the signals from the region being imaged into a desired image format. The probe may be a phased array or curved array probe, for instance, which received echo signals in a R-θ spatial format, and the scan converter will convert these signals to a Cartesian format, suitable for the display of the B mode image as pixels of a raster scanned display device. For three-dimensional imaging, scan-converted two-dimensional image data may be processed to form a 3D image by volume rendering.

In accordance with the principles of the present invention, the separated harmonic signals received from microbubbles of a contrast agent are coupled to a contrast temporal processor 50. The contrast temporal processor detects and processes the contrast signals in different ways during different stages of contrast agent wash-in as described below. The resultant contrast data values are converted into the same format as the B mode image so as to form a contrast image by a scan converter 52, which may be a separate scan converter or the same one used for B mode image scan conversion when used in a time multiplexed manner. The B mode image produced by the scan converter 42 and the contrast image produced by the scan converter 52 are coupled to an image processor 24. Since the two images are both of the same display format, the contrast image may be displayed overlaying the B mode image so that the blood flow delineated by the contrast agent is framed by the tissue structure of the B mode image. The image processor may further process the images, such as by adding graphical information, and the final image is displayed on a display device or monitor 26.

Figure 2:
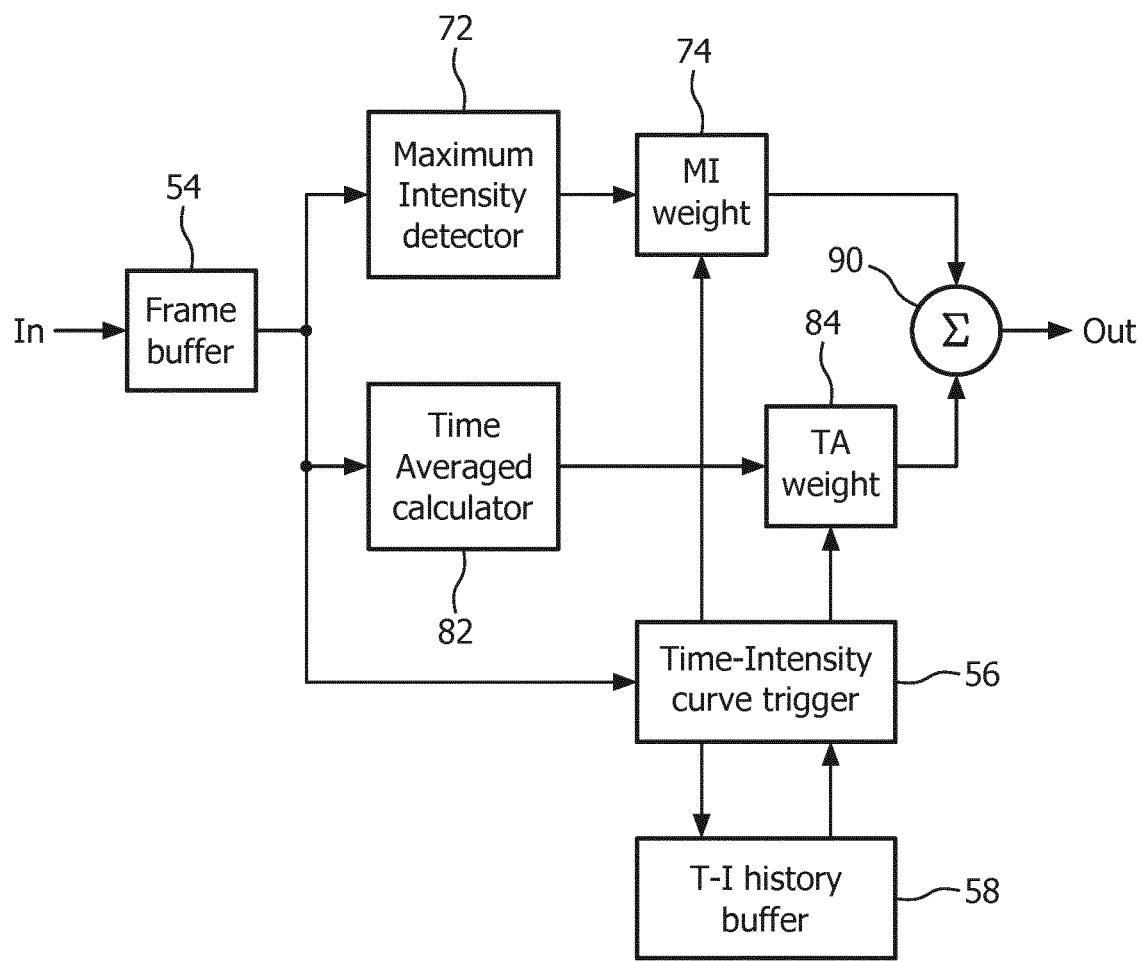
FIG. 2 is a detailed block diagram illustrating the construction and operation of the contrast temporal processor of the ultrasound system of FIG. 1.

FIG. 2 is a detailed block diagram illustrating the construction and operation of the contrast temporal processor 50. Successively received image frames are stored in a frame buffer 54. As an infused or injected contrast agent begins to arrive at the region of the body being imaged, successive image frames are stored in the frame buffer and will capture the contrast agent as it appears at progressive locations in the micro vasculature being imaged. When the probe 12 is held steady against the body of the patient, the same spatial location will appear at the same pixel location in each image. Thus, a temporal sequence of the pixel data at each unique location in the imaged region during contrast wash-in can be extracted simply by addressing the same pixel location in each of a sequence of successive images.

In accordance with the principles of the present invention, the temporal sequence of contrast data at each pixel location is processed by a maximum intensity detector 72 and a time averaged calculator 82. The maximum intensity detector receives the sequence of data values from a pixel location and compares them sequentially to detect the maximum value from the beginning of contrast wash-in to the current point in time, the most recently received contrast image value. Mathematically this can be expressed for each pixel location as $$Pmax_{x,y} = P_{max} \text{ of } P_1, P_2, P_3 \ldots P_{current}$$

where x,y is the pixel location in the image and the pixel values of frames 1, 2, 3, current from the beginning of wash-in to the current time are $P_1, P_2, P_3 \ldots P_{current}$. To give a simple example, suppose that the data values are 0, 0, 3, 2, 3, 5, 7 and 10. The value of $Pmax_{x,y}$ for this sequence would successively be 0, 0, 3, 3, 3, 5, 7 and 10. It can be seen that this detection process has a sensitivity to noise. Suppose that the first two zeroes are of the pixel value before the start of wash-in and suppose that the first of these is affected by noise or motion and is 3. The maximum intensity detected values for the sequence would then be 3, 3, 3, 3, 3, 5, 7 and 10, which undesirably reflects the noise effect.

The time averaged calculator 82, however, reduces such noise and motion effects by temporal averaging. The temporal averaging can be implemented in various ways. In an embodiment, this calculator produces a contrast pixel value which is equal to the average data value from the beginning of wash-in to the time of the current pixel. Mathematically, this can be expressed as $$Pta_{x,y} = \text{Average of } P_1, P_2, P_3 \ldots P_{current}$$

In another embodiment, the temporal averaging can be a moving average which is equal to a weighted or un-weighted average in a moving window.

It can be seen that, with this expression, momentary effects of noise will be averaged and thereby reduced over the average of the sequence of values. The operations performed by the maximum intensity detector and the time averaged calculator are repeated and their output contrast data values updated with the arrival of each new frame of contrast data in the frame buffer.

In accordance with a further aspect of the present invention, the overall time period of the contrast perfusion is separated into at least two time periods. In an embodiment, the at least two time periods can comprise a first time period and a second time period, and the contrast temporal processor produces an instantaneous contrast data value for a given pixel location which is equal to the maximum intensity value during the first time period, and which is equal to the time averaged intensity value during the second time period. For example, the contrast temporal processor can be configured to include a selector for selecting one of the maximum intensity value and the time averaged intensity value. In other embodiments, the at least two time periods can comprise a first time period, a second time period and a third time period, and the contrast temporal processor produces an instantaneous contrast data value for a given pixel location which is equal to the maximum intensity value during the first time period, and which is equal to the time averaged intensity value during the third time period, and which is equal to a combination of of the two during the second time period between the first and third time period.

In accordance with a further aspect of the present invention, the contrast temporal processor produces an instantaneous contrast data value for a given pixel location which is equal to the maximum intensity value during the initial stage of wash-in; and which is equal to the time averaged intensity value during the later stage of wash-in; and which is equal to a varying combination of the two during an intermediate stage when contrast perfusion is at a maximum. This is done by using a time-intensity (T-I) curve calculated by a time-intensity curve trigger circuit 56 for one or more contrast pixel locations. The T-I curve is a common measure of the arrival and departure of the contrast agent at a location in the body as described in U.S. Pat. No. 5,833,613 (Averkiou et al.) A time-intensity curve can be calculated for each point in an image of perfused tissue and one or more parameters of each curve extracted for use in imaging or diagnosis. For instance, a chosen parameter for each image point can be displayed in grayscale shades or color-coding to form a parametric image of perfusion as described in U.S. Pat. No. 6,692,438 (Skyba et al.) These parameters include the peak and the slope of the curves, each indicating a different characteristic of the tissue perfusion.

Figure 3:
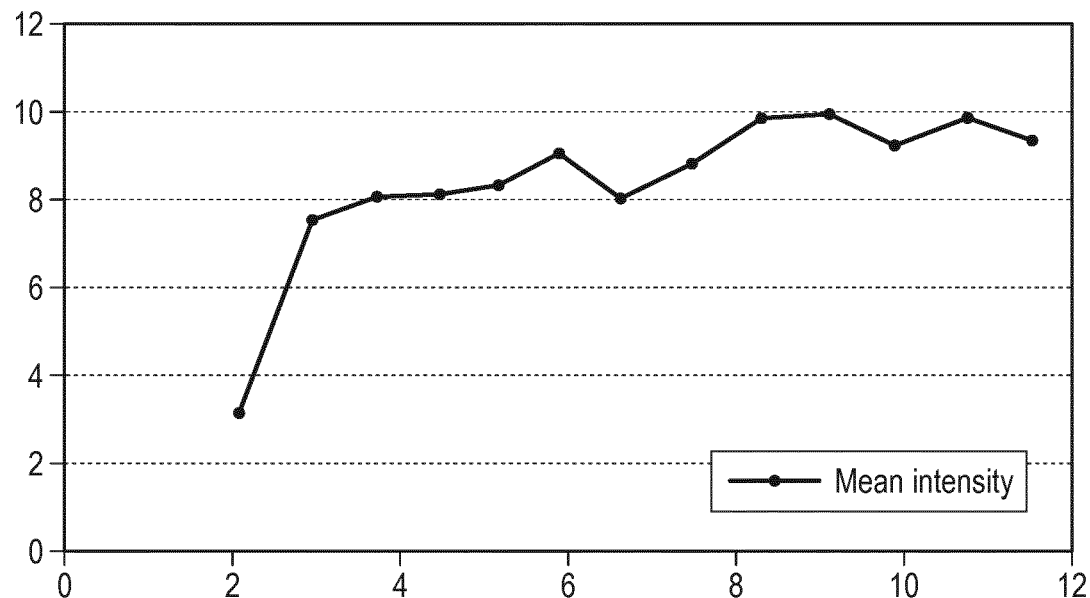
FIG. 3 is a plot of a perfusion curve of contrast pixel data during contrast perfusion at a point in the body.
Figure 4:
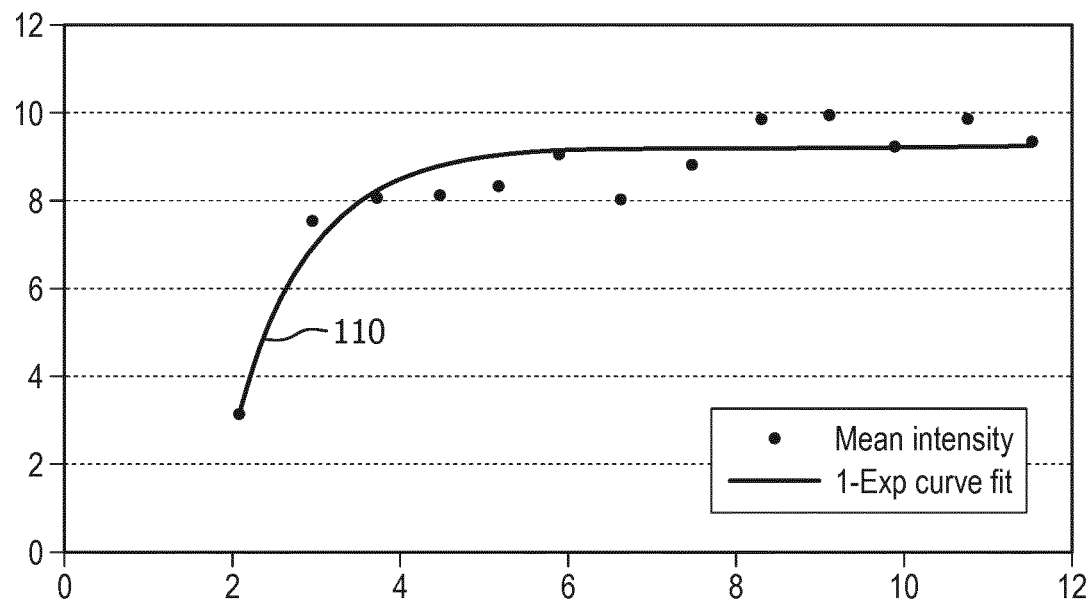
FIG. 4 illustrates the fitting of a smooth time-intensity curve to the pixel data of FIG. 3.

A perfusion curve is generally computed by measuring the intensity of the signal returned from the contrast agent as it flows into and out of the micro vasculature of the tissue. These measurements of the rise and fall of the amount of contrast agent are then fit to a curve such as that defined by the Gamma-variate curve model $$A*(x-t_0)*\exp(-\ell*(x-t_0))+C,$$

where A is the curve peak, $t_0$ is the time of initiation of the wash-in of contrast agent, $\ell$ is the slope of the rise of the curve, and x is the instantaneous measurement of the amount of the contrast agent. These time and intensity representations provide an indication to a trained clinician of the manner in which the tissue is perfused. For example, FIG. 3 shows a sequence of contrast intensity values received over time during wash-in of a contrast agent. The x-axis is the time axis and the y-axis is the amplitude (intensity) of the pixel values. These values are seen to vary somewhat erratically, as demonstrated by the line segments which connect them. To overcome this erratic variation, a curve is fit to the intensity data values as shown by curve 110, using a curve-fitting equation such as that given above. This presents a much smoother representation of the wash-in of contrast, and it is the fitted curve which is analyzed to yield the parameters enumerated above.

Figure 5:
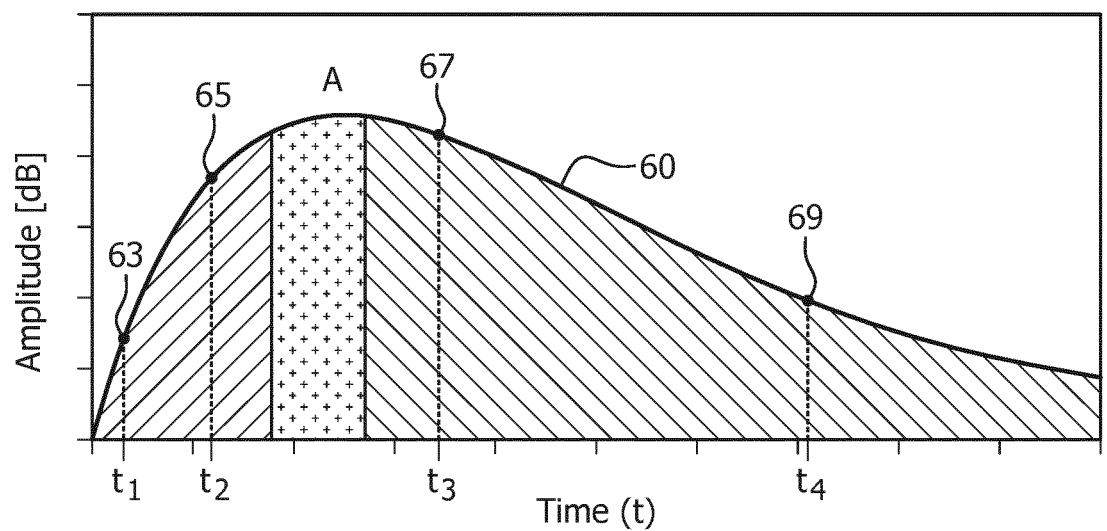
FIG. 5 illustrates an idealized contrast agent time-intensity curve segmented into three time periods.
Figure 6:
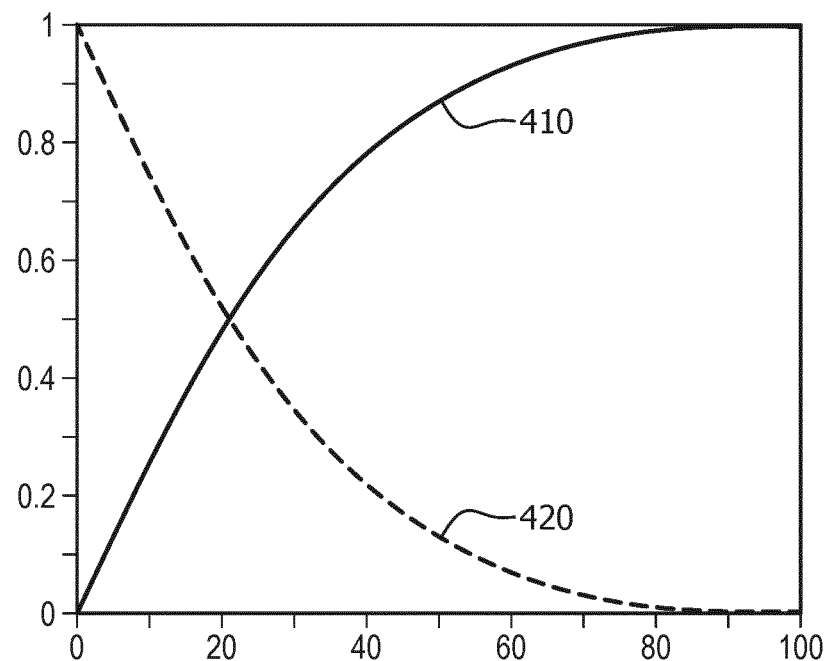
FIG. 6 illustrates weighting characteristics used to weight both maximum intensity detection and time-averaged processing during the peak enhancement stage of contrast perfusion in accordance with the principles of the present invention.

FIG. 5 shows an exemplary T-I wash-in curve 60 resulting from curve-fitting. In this example, the rise or initial wash-in stage is the time duration following a rise of 20% of the peak A of the curve 60, indicated by 63 and time $t_1$, to a level of 80% of the peak of the curve as indicated by 65 and time $t_2$. The enhancement stage when the amount of contrast agent is around its peak of perfusion is the time duration between the 80% mark of 65 at time $t_2$ and a decline to 90% of the peak at 67 and time $t_3$. The decline of contrast or wash-out stage is the time duration from 90% of the peak at 67 and time $t_3$ to 30% of the peak at 69 and time $t_4$. In this example, $t_1$-$t_2$ is the wash-in stage, $t_2$-$t_3$ is the enhancement stage, and $t_3$-$t_4$ is the wash-out stage. In accordance with the principles of the present invention, the values produced by the maximum intensity detector 72 are used as the instantaneous contrast pixel values during the initial stage of wash-in, the period of time up to 65 ($t_2$) in the drawing. The values produced by the time averaged calculator 82 are used in the latter stage, the period of time following 67 ($t_3$). During the peak enhancement stage $t_2$-$t_3$, a weighted combination of both values is used. This is done by triggering weighting changes by the time-intensity curve trigger circuit 56 when the respective stages are attained, which controls the operation of two weighting circuits, a maximum intensity (MI) weighting circuit 74 and a time averaged (TA) weighting circuit 84. These weighting circuits apply weights to the respective values such as those indicated by weighting function curves 410 and 420 of FIG. 6. In this example, curve 420 is used by the TA weighting circuit 84 and curve 410 is used by the MI weighting circuit 74.

To give an example of this operation, suppose that the maximum intensity detector 72 and the time averaged calculator 82 are producing detected and calculated contrast values throughout the wash-in, wash-out period. Initially the MI weighting circuit 74 is weighting maximum intensity values with a weight of one, and the TA weighting circuit is weighting time averaged values with a weight of zero. This means that an output summer 90 is receiving only fully weighted maximum intensity values. The sequence of output values produced by the summer will thus be maximum intensity values which fully reflect the rapid rise in contrast intensity during this initial stage. At time $t_2$ in FIG. 5, the time-intensity curve trigger circuit 56 triggers the weighting circuits to begin using the respective curve functions of FIG. 6. The weighting of the maximum intensity values by the MI weighting circuit 74 will thus begin to decline from one toward zero from time $t_2$ to time $t_3$, and the weighting of the time averaged values by the TA weighting circuit 84 will begin to increase from zero toward one. The summer 90 output will thus be a weighted combination of both values, initially dominated by the maximum intensity but decreasing and progressively reflecting the increasing contribution of the time averaged value until, at time $t_3$, the weighting of the maximum intensity value has reached zero and the weighting of the time averaged value has reached one. Thereafter, the contrast values will only be time average calculated values, which will exhibit diminished adverse effects due to noise and motion.

It will be understood that it is not possible to accurately predict the peak A of a time-intensity curve during calculation of a first time-intensity curve before the peak has been realized. To resolve this problem, the illustrated implementation of the present invention also has a T-I history buffer 58 to store T-I parameters from one curve which are used until a new T-I curve is calculated. As an example, suppose that the patient is being infused with a steady flow of contrast. A high power flash transmission of ultrasound is applied to the image region to destroy the microbubbles in the region. Thereafter, during a new influx of microbubbles, a time-intensity curve is calculated and produced, and times $t_2$ (end of initial wash-in) and $t_3$ (end of peak enhancement) are determined and stored in the T-I history buffer. Another high power flash transmission is applied to the image region and a new influx of contrast begins to wash into the imaged micro vasculature. As the microbubbles begin to arrive and build in intensity at the pixel locations in the image, the weighting circuits are triggered to change their weights at times $t_2$ and $t_3$ as previously determined. During the same wash-in period, the time-intensity curve trigger circuit is calculating a new time-intensity curve and determining updated times $t_2$ and $t_3$ using the current wash-in, wash-out cycle and storing the updated values in the T-I history buffer. Thus, each repeated wash-in, wash-out cycle uses the most recently updated set of $t_2$ and $t_3$ switchover times to trigger the changing of the weighting circuit functions.

Figure 7:
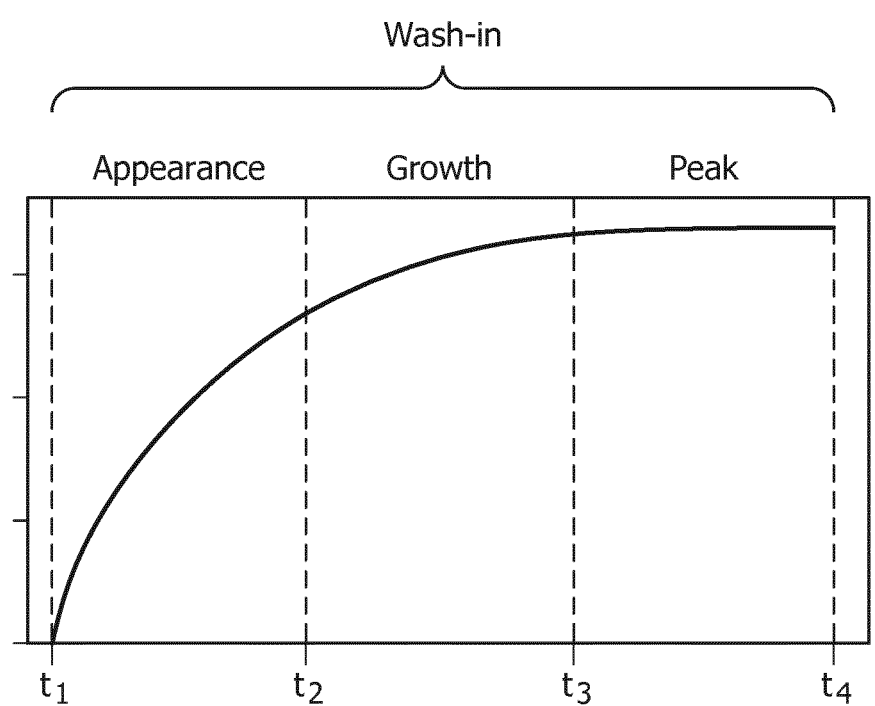
FIG. 7 illustrates an alternative approach for segmenting an idealized contrast agent time-intensity curve.

FIG. 7 shows a different approach from FIG. 5. In this example, $t_1$-$t_2$ is the appearance stage, $t_2$-$t_3$ is the growth stage, and $t_3$-$t_4$ is the peak stage. In accordance with the principles of the present invention, the values produced by the maximum intensity detector 72 are used as the instantaneous contrast pixel values during the appearance stage. The values produced by the time averaged calculator 82 are used in the peak stage. During the growth stage $t_2$-$t_3$, a weighted combination of both values is used. This is done by triggering weighting changes by the time-intensity curve trigger circuit 56 when the respective stages are attained, which controls the operation of two weighting circuits, a maximum intensity (MI) weighting circuit 74 and a time averaged (TA) weighting circuit 84. These weighting circuits apply weights to the respective values such as those indicated by weighting function curves 410 and 420 of FIG. 6. In this example, curve 420 is used by the TA weighting circuit 84 and curve 410 is used by the MI weighting circuit 74. It will be appreciated that one location in an image where contrast agent is present can be used to calculate the time-intensity curve to be used to trigger the changing weighting functions for every pixel in the image. Alternatively, T=I curves can be calculated at several locations in an image, and an average of the $t_2$ and $t_3$ times measured at each location can be used by the time-intensity curve trigger circuit to trigger a changeover of the weighting functions. Given sufficient computing power, it is also possible to compute a time-intensity curve at each pixel location in an image field and use the T-I curve for each pixel location to determine the switchover of the weighting circuits for each unique pixel location.

One skilled in the art will immediately recognize that an ultrasound system in accordance with the present invention can be constructed using hardware, software, or a combination of both. In a hardware configuration the system can contain circuitry performing the described invention, or use advanced digital circuitry such as an FPGA with gates configured to perform the claimed processing. In a software configuration, which is how today's ultrasound systems are largely constructed, the frame buffer is a digital memory storing the contrast data in addressable memory locations, and the other functionality shown in FIG. 2 is performed by software subroutines. The maximum intensity detector, for instance, is provided by a software routine performing comparisons by subtraction of successively addressed contrast data values from the digital memory. The time averaged calculator is provided by a software routine which adds a sequence of contrast data values and divides the sum by the number of values. The weighting circuit function is provided by multiplying the values from the detector and calculator routines by weighting coefficients stored in memory as triggered by the time-intensity curve trigger. The summer is provided by an adding subroutine. The time-intensity curve trigger fits a T-I curve to the contrast data values with a routine that executes the T-I equation given above by iteratively executing the equation with different variable values until the best fit is found. The T-I history buffer is a digital memory. Following the summer 90, the output data can be normalized if desired by multiplying the output data by gain coefficient values. Combinations of both hardware and software will be readily apparent to those skilled in the art.

The invention claimed is:

1. An ultrasonic diagnostic imaging system for contrast enhanced imaging of micro vasculature in an image region, comprising:

an ultrasound probe configured to transmit ultrasonic beams and receive ultrasonic echo signals;

a beamformer configured to beamform the echo signals to produce coherent echo signals;

a signal separator responsive to the coherent echo signals and configured to produce separated harmonic echo signals received from the contrast agent;

a contrast temporal processor responsive to the harmonic echo signals and configured to process harmonic signals received from a contrast agent to produce a contrast data value for each of a plurality of spatial locations in the imaging region for a time point in a time period, the contrast value for a spatial location in the image region being produced in different ways over the time period, the time period including at least a wash-in stage of the contrast agent, the contrast temporal processor comprising a maximum intensity (MI) detector and a time averaged (TA) calculator configured to process the harmonic echo signals to produce differently processed contrast data values, an MI weighting circuit configured to weight contrast data values produced by the maximum intensity detector, and a TA weighting circuit configured to weight contrast data values produced by the time averaged calculator, and a summer configured to sum the weighted contrast data values;

a scan converter coupled to receive the produced contrast data values and configured to produce a contrast image for the time point by arranging the produced contrast data values for the plurality of spatial locations for the time point in a desired image format; and a display coupled to the scan converter and configured to display a contrast image.

2. The ultrasonic diagnostic imaging system of claim 1, further comprising a frame buffer configured to store harmonic echo signals received from the signal separator.

3. The ultrasonic diagnostic imaging system of claim 2, wherein the contrast temporal processor further comprises a time-intensity curve trigger circuit, responsive to harmonic echo signals from the framebuffer, configured to produce a time-intensity curve of successive stages of contrast wash-in.

4. The ultrasonic diagnostic imaging system of claim 3, wherein the time-intensity curve demarcates an initial wash-in stage and a later wash-out stage, and wherein the time-intensity curve triggers the MI weighting circuit and the TA weighting circuit to produce maximum intensity contrast values during the initial stage and time averaged contrast values during the later stage.

5. The ultrasonic diagnostic imaging system of claim 4, wherein the time-intensity curve further demarcates an intermediate stage following the initial stage, and wherein the time-intensity curve triggers the MI weighting circuit and the TA weighting circuit to produce the maximum intensity contrast values and the time averaged contrast values during the intermediate stage; and wherein the summer is configured to produce a combination of the maximum intensity contrast values and the time averaged contrast values during the intermediate stage.

6. The ultrasonic diagnostic imaging system of claim 5, wherein the MI weighting circuit is configured to utilize a declining weighting function during the intermediate stage; and wherein the TA weighting circuit is configured to utilize an increasing weighting function during the intermediate stage.

7. The ultrasonic diagnostic imaging system of claim 3, wherein the contrast temporal processor further comprises a Time-Intensity (T-I) history buffer configured to store parameters of the T-I curve produced by the time-intensity curve trigger circuit.

8. The ultrasonic diagnostic imaging system of claim 7, wherein the time-intensity curve trigger circuit is configured to utilize parameters stored during a first contrast wash-in period to trigger the weighting circuits during a second contrast wash-in period.

9. The ultrasonic diagnostic imaging system of claim 8, wherein the parameters comprise a first parameter $t_2$ demarcating an end of an initial wash-in stage and a second parameter $t_3$ demarcating a beginning of a later wash-out stage.

10. The ultrasonic diagnostic imaging system of claim 1, wherein the signal separator is further configured to produce separated fundamental frequency echo signals, and the system further comprises:
- a B mode detector responsive to fundamental frequency echo signals and configured to produce detected B mode signals;
- the scan converter responsive to the detected B mode signals and configured to produce a B mode image in the desired image format; and
- an image processor, responsive to the contrast image and the B mode image and configured to produce an image comprising a combination of the B mode image and the contrast image.

11. The ultrasonic diagnostic imaging system of claim 3, wherein the time-intensity curve demarcates an appearance stage, a growth stage, and a peak stage, and
- wherein the time-intensity curve triggers the MI weighting circuit and TA weighting circuit to produce the maximum intensity contrast values during the appearance stage, the time averaged contrast values during the peak stage, and a mixture of maximum intensity contrast values and time averaged contrast values during the growth stage.

12. An apparatus for producing an ultrasound contrast image of micro vasculature in an image region, comprising:
- a contrast temporal processor responsive to harmonic echo signals and configured to process harmonic signals received from a contrast agent to produce a contrast data value for each of a plurality of spatial locations in the imaging region for a first time point and a second time point in a time period, the first time point being different from the second time point, the contrast data value for a spatial location in the image region for the first time point being produced in different ways from the way to produce the contrast value for the spatial location for the second time point, the time period including at least a wash-in stage of the contrast agent, the contrast temporal processor comprising
  - a maximum intensity (MI) detector and a time averaged (TA) calculator configured to process the harmonic echo signals to produce differently processed contrast data values,
  - an MI weighting circuit configured to weight contrast data values produced by the maximum intensity detector, and a TA weighting circuit configured to weight contrast data values produced by the time averaged calculator, and
- a summer configured to sum the weighted contrast data values; and
- a scan converter coupled to receive the produced contrast data values and configured to produce a contrast image for the first time point by arranging the produced contrast data values for the plurality of spatial locations for the first time point in a desired image format, and to produce a contrast image for a second time point by arranging the produced contrast data values for the plurality of spatial locations for the second time point in a desired image format.

* * * * *